United States Patent
Golini

(10) Patent No.: US 9,968,581 B2
(45) Date of Patent: May 15, 2018

(54) CETYLATED FATTY ACID AND ALKALI BUFFERED CREATINE ANTI-INFLAMMATORY COMPOSITION

(71) Applicant: Jeffrey M. Golini, Billings, MT (US)

(72) Inventor: Jeffrey M. Golini, Billings, MT (US)

( * ) Notice: Subject to any disclaimer, the term of this patent is extended or adjusted under 35 U.S.C. 154(b) by 0 days. days.

(21) Appl. No.: 14/120,457

(22) Filed: May 20, 2014

(65) Prior Publication Data

US 2015/0011631 A1    Jan. 8, 2015

Related U.S. Application Data

(63) Continuation of application No. 12/806,436, filed on Aug. 12, 2010.

(60) Provisional application No. 61/274,175, filed on Aug. 13, 2009.

(51) Int. Cl.
| | | |
|---|---|---|
| *A01N 43/00* | (2006.01) | |
| *A61K 31/33* | (2006.01) | |
| *A61K 31/231* | (2006.01) | |
| *A61K 31/197* | (2006.01) | |
| *A61K 31/23* | (2006.01) | |

(52) U.S. Cl.
CPC .......... *A61K 31/231* (2013.01); *A61K 31/197* (2013.01); *A61K 31/23* (2013.01)

(58) Field of Classification Search
CPC .................................................... A61K 31/231
USPC ........................................................ 514/183
See application file for complete search history.

(56) References Cited

U.S. PATENT DOCUMENTS

| | | | |
|---|---|---|---|
| 6,159,485 A | 12/2000 | Yu et al. | |
| 6,168,802 B1 | 1/2001 | Howard et al. | |
| 6,274,161 B1 | 8/2001 | Howard et al. | |
| 6,399,661 B1 * | 6/2002 | Golini | ........................... 514/565 |
| 2003/0212130 A1 | 11/2003 | Miller et al. | |
| 2006/0062849 A1 | 3/2006 | Byrd | |
| 2006/0216251 A1 | 9/2006 | Morariu | |
| 2009/0005450 A1 | 1/2009 | Nivaggioli | |
| 2009/0105196 A1 | 4/2009 | Nivaggioli | |
| 2009/0137669 A1 | 5/2009 | Miller et al. | |

FOREIGN PATENT DOCUMENTS

| | | |
|---|---|---|
| CN | 200910196183 | 3/2010 |
| WO | WO 03049687 A2 * | 6/2003 |
| WO | WO2004/071406 | 8/2004 |

OTHER PUBLICATIONS

Kraemer et al. (Effect of a cetylated fatty acid topical cream on functional mobility and quality of life of patients with osteoarthritis. The Journal of Rheumatology. 2004. vol. 31, No. 4; p. 767-774).*
WO 01/41783 A1 (Levin Bruce [US]), Jun. 14, 2001, claims.
WO 2004/071406 A2 (Univ Nebraska [US]); Miller Donald W [US]; Augustine Samuel C [US]; WAG) Aug. 26, 2004, claims.
US 2003/212130 A1 (Miller Donald W [US] et al) Nov. 13, 2003, claims.
WO 02/02075 A1 (Beiersdorf AG [DE]; Blatt Thomas [DE]; Schmidt Melanie [DE]; Schreiner) Jan. 10, 2002, p. 1, paragraph 1.
Nomura Akihiro et al: "Anti-inflammatory activity of creatine supplementation in endothelial cells in vitro.", British Journal of Pharmacology, vol. 139, No. 4, Jun. 2003, pp. 715-720, XP002611589, ISSN: 0007-1188, abstract.
US 6 677 321 B1 (Levin Bruce [US]) Jan. 13, 2004, col. 1, line 53-col. 1, line 63.
US 7 772 279 B2 (Leonard Edward C [US]) Jan. 13, 2004, col. 1, line 53-col. 1, line 63.
WO 00/64436 A1 (CG and Associates [US]; Lord Gary R [US}; Lytle Carol D [US], Nov. 2, 2000, claims.
US 4 113 881 A (Diehl Harry Weldon) Sep. 12, 1978, claims.

* cited by examiner

*Primary Examiner* — Layla Soroush
(74) *Attorney, Agent, or Firm* — Seed IP Law Group LLP

(57) ABSTRACT

An anti-inflammatory composition for treatment of inflamed joints. This composition includes an alkali buffered creatine and a cetylated fatty acid. The composition can be used for treating inflammation either by oral ingestion or by topical treatment.

5 Claims, No Drawings

CETYLATED FATTY ACID AND ALKALI BUFFERED CREATINE ANTI-INFLAMMATORY COMPOSITION

This application claims the benefit of provisional application Ser. No. 61/274,175 filed Aug. 13, 2009.

BACKGROUND OF INVENTION

The present invention refers to a composition composed of a cetylated fatty acid and alkali buffered creatine for reducing joint and muscle related inflammation.

Chronic inflammation and muscle pain affects the body's ability to execute fluid motion. Ensuing joint stiffness restricts range of motion (ROM), which in turn negatively impacts quality of life (QOL). Chronic inflammation is a primary reason for doctor visits and increased costs in our healthcare system. Thousands of "Baby Boomers" born between 1946 and 1950, are now transitioning through age 60 and beyond. Along with the prospect of living to the century mark, comes the reality that osteoarthritis, sports and non-sports related injuries also increase. This year, the Arthritis Foundation has estimated that immune-related joint degenerative conditions are expected to strike more than 27 million Americans during the next decade, with additional untold numbers afflicted with ligament weakness, fibromyalgia, idiopathic pains and muscle trauma. Pain reducing medications are utilized daily, essentially to combat the symptoms of immune-related aging issues. Unfortunately, prescription drugs are not without side effects and many consumers are turning or have already turned to over-the-counter (OTC) substances in the hopes of obtaining pain relief without those side effects.

It has been found that creatine is helpful in reducing inflammation as discussed in United States Publication No. 2009/0137669. Further, cetylated fatty acids have been reported to exhibit anti-inflammatory activity in joint and muscle regions.

It would be desirable to provide a composition which would deliver cetylated fatty acids and alkali buffered creatine to a joint for treating inflammation.

SUMMARY OF INVENTION

The present invention relates to an anti-inflammatory composition for treatment of inflamed joints. This composition includes an alkali buffered creatine and a cetylated fatty acid. The composition can be used for treating inflammation either by oral ingestion or by topical treatment.

DESCRIPTION OF A PREFERRED EMBODIMENT

The present invention relates to an oral, alkali buffered creatine and cetylated fatty acid composition for reducing joint and muscle inflammation. When taken orally, the fatty acids bonded with the creatine get into the bloodstream and are delivered to the inflamed joint. The cell lipid structure surrounding the joint are lubricated by the fatty acids allowing the creatine to work more effectively in reducing inflammation.

A preferred embodiment of the present invention utilizes an alkalyn buffered creatine sold under the trade name Kre-Alkalyn® by All American Pharmaceutical and Natural Foods Corporation. This creatine is then mixed, bonded, reacted or compounded with a cetylated fatty acid as follows:

Typical Formulation:

Formulation 1:

| | |
|---|---|
| Kre-Alkalyn7 creatine | 500 mg |
| Soy Bean Oil | 250 mg |
| Cetyl Myristoleate | 250 mg |

The Kre-Alkalyn® creatine is an alkalyn buffered creatine. The soybean oil is a fatty acid and is used as a base. The cetyl myristoleate is a member of the cetylated fatty acid family.

Clinical tests were performed to determine the efficacy of this formulation.

Clinical Tests:

Objectives: Determine if a unique oral, alkali buffered-creatine B cetylated fatty acid composition (Kre-1), (a) is capable of reduce chronic joint and muscle related inflammation/pain, (b) can address site-specific pain with equal effectiveness, and, (c) will increase range of motion (ROM) in the afflicted area.

Design: A total of 35 subjects (21 males, 14 females), each experiencing isolated areas of joint/muscle inflammation/pain, were divided into 2 groups: Group A was assigned four capsules of Kre-1 daily, Group B, an equal number of placebo capsules. The duration of the study was 30 days.

Settings/Location: Participants entrance and exit interviews were conducted in the conference center at the All American Pharmaceutical. Study information (informed consent, test and placebo materials) was provided by an administrative assistant at All American Pharmaceutical. Pre and post blood tests (creatinine, AST, C-reactive protein) were accomplished at a local Laboratory Corporation of America blood lab. Physical examinations (entrance and exit), blood pressures, ROM, target area tenderness assessments, scoring and review of personal >Pain Journals=by the test subjects and physicians were conducted at the Yellowstone Naturopathic Clinic, in Billings, Mont.

Subjects: Group A (n=24; age 55 +/−32 yrs.) received Kre-1, and >Group B=(n=11; age 45 +/−15 yrs.) received the placebo.

Results: Data indicated approximately: 100% of ankle and foot pain, 80-85% of neck, shoulder, elbow, wrist, and hand pain, 71% of knee pain, respondents rated Kre-1 better than/as good as a prescription product in its ability to reduce/eliminate pain. Hip and back pain scores were no better than placebo scores for the same areas. >Group A=experienced a modest increase in mobility (35%), but no measurable increase in ROM over that experienced in the placebo group (Group B).

Conclusions: Kre-1 exerts it greatest impact on areas of inflammation/pain in the extremities, as well as in the neck and shoulder region.

TABLE 1

Oral Kre-1 for Joint and Muscle Inflammation B Study Data

| | Group A (Kre-1) | Group B (Placebo) |
|---|---|---|
| Participants: | | |
| Initial | 24 | 11 |
| Completing | 20 (21)* | 11 |
| Gender | 17 males/3 females | 4 males/7 females |
| Age | 23 B 88 years | |
| Drop outs (M/F) | 3 F | 0 |

| | Overall average | | |
|---|---|---|---|
| Entrance blood tests: | | | |
| creatinine | 0.9 mg/dl | 0.8 mg/dl | 23 IU/L |
| AST(SGOT) | 4.1 mg/dl | 6.2 mg/dl | 22 IU/L |
| C-reactive Protein | | | |
| Exit blood tests: | | | |
| creatinine | 0.9 mg/dl | 0.8 mg/dl | |
| AST(SGOT) | 25 IU/L | 21 IU/L | |
| C-reactive Protein | 4.2 mg/L | 5.1 mg/L | |

| | Per Area: | | |
|---|---|---|---|
| Pain Relief: | | | |
| Percentage of participants rating their treatment, as good as or better than their usual OTC or prescription pain reliever | Ankle/Foot B | 100% (2/2) | 0% |
| | Knee (and leg) B | 71+% (5/7) | 0% |
| | Hip B | 33% (1/3) | 33% (1/3) |
| | Back B | 50% (5/10) | 0% |
| | Neck/Shoulders B | 85+% (6/7) | 33% (1/3) |
| | Elbow/Wrist/Hand | 80% (4/5) | 33% (1/3) |
| No Pain Relief: | | | |
| Percentage of participants rating their treatment, not as good as or didn't work compared to their usual OTC or prescription pain reliever | Ankle/Foot B | 0% | 100% (3/3) |
| | Knee (and leg) B | 29% (2/7) | 100% (5/11) |
| | Hip B | 67% (2/3) | 66% (2/3) |
| | Back B | 50% (5/10) | 100% (1/1) |
| | Neck/Shoulders B | 15% (1/7) | 66% (2/3) |
| | Elbow/Wrist/Hand | 20% (1/5) | 66% (2/3) |

| | Overall Average | | | |
|---|---|---|---|---|
| | Yes | No | Yes | No |
| Personally said they experienced reduced pain/increased mobility | 60% (12/20) | 40% (8/20) | 27% (3/11) | 73% (8/11) |

| | | Overall Average | |
|---|---|---|---|
| Blood Pressure: | | | |
| Entrance | Systolic/Diastolic | 127/83 | 129/82 |
| Exit | Systolic/Diastolic | 125/75 | 119/77 |

*This participant withdrew before the end of the study.

TABLE 2

Kre-1 for Joint and Muscle Inflammation B Physicians Reports

| | Group A (Kre-1) | Group B (Placebo) |
|---|---|---|
| Pain: | | |
| Decrease | 90% (18/20) | 36% (4/11) |
| No Change | 10% (2/20) | 55% (6/11) |

The results of this study show that a combination of a cetylated fatty acid and an alkalai buffered creatine provides an effective non-prescription material for reduction of pain and stiffness of the extremities, neck and shoulder regions in humans. It is intended that members of the cetylated fatty acid family including cetyl myristoleate, cetyl mylistate, cetyl palmitoleate, cetyl laureate, cetyl palmitate and cetyl oleate could be used equally as well. The cetylated fatty acids have anti-inflammatory properties with the ability to suppress pro-inflammatory cytokines. The alkali buffered creatine positively affects endothelial permeability, thereby inhibiting potentially inflammatory stimulating molecules from adhering and expressing their action as endothelial cells.

Delivery of the creatine/fatty acid composition may preferably occur through ingestion. It is contemplated that the creatine/fatty acid composition may be formulated such as a liquid drink and allow for oral ingestion. Further, the creatine/fatty acid composition may be formulated including solid formulations such as granules, a tablet, a capsule and the like for oral ingestion. Further, a food supplement such as a sports bar, and the like, may be employed for delivery of the creatine/fatty acid composition.

In addition, other formulations such as an emulsion, suspension and the like may be employed and allow delivery of the creatine/fatty acid composition to an inflamed joint. These formulations allow application through a variety of methods such as topical applications including ointments, lotions, creams and gels.

While the fundamental novel features of the invention have been shown and described, it should be understood that various substitutions, modifications, and variations may be made by those skilled in the arts, without departing from the spirit or scope of the invention. Accordingly, all such modifications or variations are included in the scope of the invention as defined by the following claims:

I claim:

1. A method of treating either or both of joint inflammation and muscle inflammation in a patient, comprising orally administering to the patient having either or both of joint inflammation and muscle inflammation a therapeutically effective amount of a composition consisting essentially of an alkali buffered creatine and a cetylated fatty acid.

2. The method of claim 1 wherein the cetylated fatty acid is selected from the group consisting of cetyl myristoleate, cetyl mylistate, cetyl palmitoleate, cetyl laureate, cetyl palmitate, cetyl oleate and mixtures thereof.

3. The method of claim 1 wherein the cetylated fatty acid is cetyl myristoleate.

4. The method of claim 1 wherein the patient has joint inflammation.

5. The method of claim 1 wherein the patient has muscle inflammation.

* * * * *